United States Patent [19]
Irwin

[11] 3,986,402
[45] Oct. 19, 1976

[54] LIQUID SAMPLING
[75] Inventor: Malcolm F. Irwin, West Chester, Pa.
[73] Assignee: Pro-Tech Inc., Malvern, Pa.
[22] Filed: Sept. 29, 1975
[21] Appl. No.: 617,648

[52] U.S. Cl. ............................. 73/421 R; 73/423 R
[51] Int. Cl.² .......................................... G01N 1/18
[58] Field of Search .......... 73/421 R, 421 A, 421 B, 73/423 R, 424

[56] References Cited
UNITED STATES PATENTS

| | | | |
|---|---|---|---|
| 2,625,952 | 1/1953 | Eide et al. | 73/421 A X |
| 3,509,770 | 5/1970 | Morton | 73/423 R X |
| 3,561,273 | 2/1971 | Tanila | 73/423 R |
| 3,583,235 | 6/1971 | Tanila | 73/423 R |
| 3,751,990 | 8/1973 | Blechman | 73/423 R |
| 3,788,145 | 1/1974 | Irwin | 73/421 B |

FOREIGN PATENTS OR APPLICATIONS 19,223   8/1910   United Kingdom .............. 73/423 R

*Primary Examiner*—Richard C. Queisser
*Assistant Examiner*—Joseph W. Roskos

[57] ABSTRACT

Liquid samples are collected simultaneously by intermittent diversion of a stream withdrawn from a body of liquid to be sampled and passed by a diversion locus into a splitting region having multiple outlets. The liquid is prevented from flowing through the outlets during periods of diversion, and upon completion of such period the outlets are opened to pass liquid streams therefrom. This multipleoutlet confining region is embodied in the sample compartment of a diverter chamber, and the valving includes a horizontally movable slide adapted to close off and to open up all the outlets in unison.

13 Claims, 6 Drawing Figures

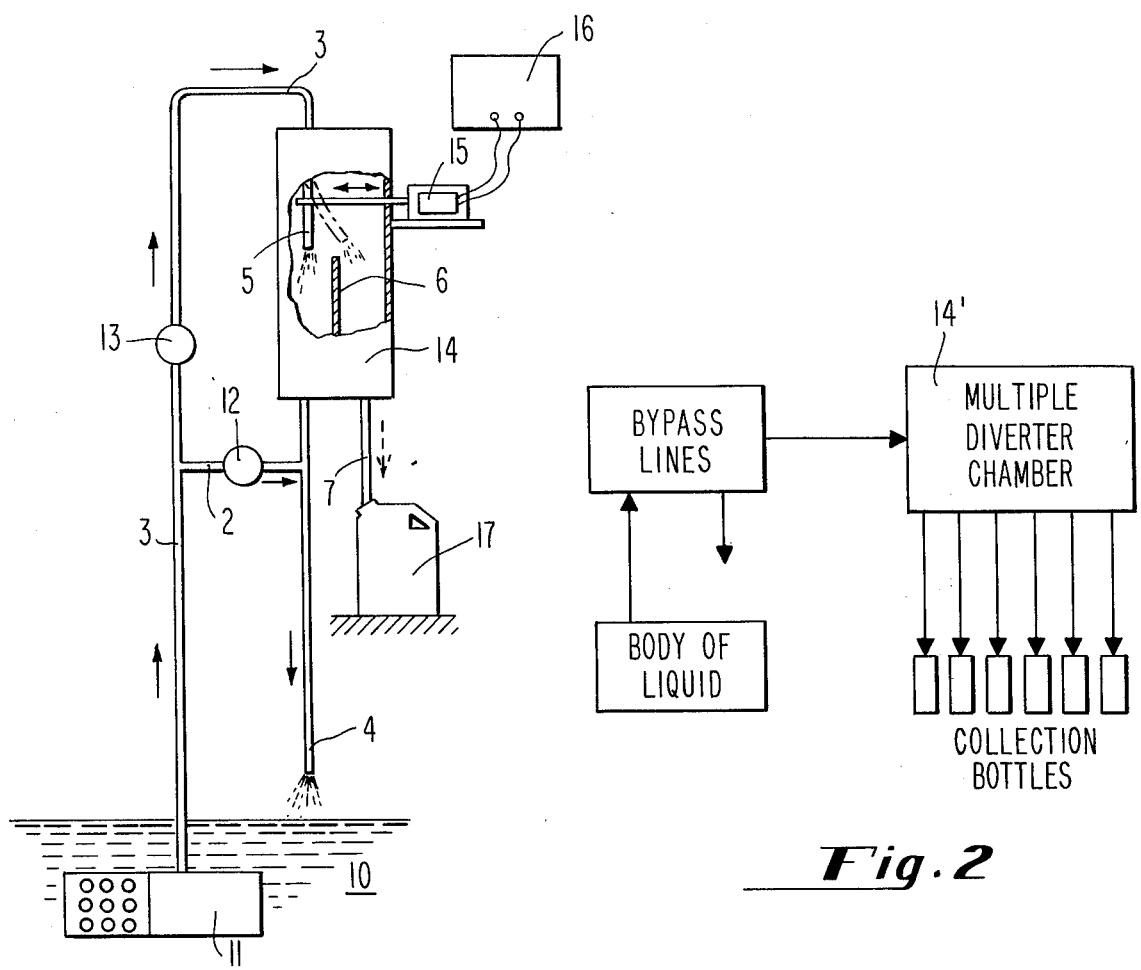
*Fig.1*
*Fig.2*
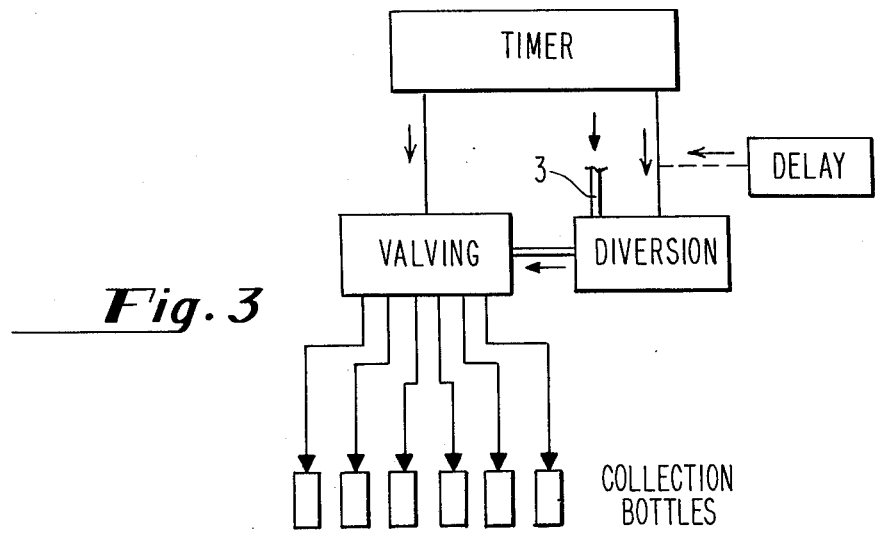
*Fig.3*

LIQUID SAMPLING

This invention relates to liquid sampling, especially the sampling of liquid to provide a plurality of like samples simultaneously.

Increasing emphasis upon quality of the environment has given rise to increased sampling of liquids for determination of composition, particularly component contaminants or pollutants. Analysis for more than one component necessitates more than one sample, or at least more than one portion of the same sample. Once a sample is in a collection container, however, a portion decanted from it is very likely to differ a good deal from what is left behind in the container, and successive decanting is almost certain to provide a final fraction that is quite different from the initially decanted fraction. For this reason alone, simultaneous collection of like samples is appropriate and may be required.

Some types of pollutant change in concentration or composition (or both) in a collection bottle at ordinary temperatures and should be inhibited from changing if subsequent analysis is to reflect accurately the condition that prevailed in the liquid when it was sampled. As various inhibitors can affect one another or an inhibitor for one component may alter the concentration of another component, separate sample collection bottles are necessary to accommodate the respective inhibitors.

A primary object of the present invention is provision of a plurality of like samples simultaneously.

Another object is collection of simultaneous samples alike except for desired differences in sample volume.

A further object is provision of apparatus for accomplishing the foregoing objects.

Other objects of this invention, together with means and methods for attaining the various objects, will be apparent from the following description of a preferred embodiment of the invention, which is presented by way of example rather than limitation.

FIG. 1 is a schematic side elevation of apparatus providing background for this invention;

FIG. 2 is a block diagram of an embodiment of the present invention;

FIG. 3 is a block diagram showing timing interconnections of the invention;

Figure 4:
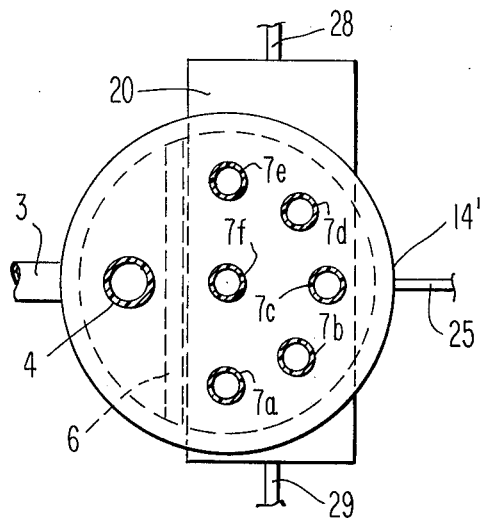
FIG. 4 is a schematic bottom sectional plan of apparatus embodying the invention.

In general, the objects of the present invention are accomplished, in liquid sampling wherein liquid is withdrawn from a body of liquid being sampled to flow past an intermittent diversion locus and back to the body of liquid or to waste except when being diverted from such locus to a collection location, for the purpose of providing a plurality of separate samples simultaneously, comprising diverting the flow of liquid temporarily into a region of confinement, providing a plurality of outlets from such confinement, and separately flowing streams of liquid from the respective outlets to the collection location and collecting them as individual samples thereat.

In apparatus terms the invention is directed to improved means for collecting multiple samples comprising a device for diverting the liquid flow intermittently into a temporarily confining chamber, the chamber having a plurality of outlets therefrom to individual containers, and valve means for closing and opening the outlets.

FIG. 1 shows a conventional flow-through type of liquid sampler in which submersible pump 11 with intake screen under the surface of body of liquid 10 has flow line 3 leading to diverter chamber 14 of the sampler. Bypass line 2 with bypass valve 12 interconnects the flow line to return or waste line 4, shown as discharging from the diverter chamber back into the body of liquid to complete the bypass path. Trim valve 13 in the portion of flow line 3 cooperates with the bypass valve in precluding an excessive flow rate into the diverter chamber.

Flexible inlet tube 5 in diverter chamber 14 normally is oriented vertically (as shown in solid lines) to discharge into a primary compartment at the left of baffle 6 rising vertically from the bottom of the chamber, whereupon the discharged liquid drains from the chamber via return or waste line 4 connected to an outlet (not separately shown) at the bottom left of the chamber. Alternatively, whenever timer 16 (or an alternative timing source) actuates solenoid 15, inlet tube 5 is flexed temporarily to the right to discharge into a secondary compartment, at the right of baffle 6, from which the discharged liquid drains via sample line 7 into sample collection bottle 17. Cessation of the timing signal deactivates the solenoid, releasing the inlet tube to its normally vertical position for discharge to waste.

FIG. 2 shows in block form the lines, here called Bypass Lines, shown in more detail in the preceding view, and interconnected Multiple Diverter Chamber 14' replacing individual diverter chamber 14 of the preceding view. The multiple diverter chamber is shown with a half dozen outlets leading individually to a corresponding number of Collection Bottles, in contrast to the single bottle shown previously.

FIG. 3 shows schematically a Timer connected to actuate both Diversion of the liquid stream in the diverter chamber and Valving of the outlets therefrom to the Collection Bottles. Flow line 3 is shown fragmentarily as a vertical double line leading to the diversion locus. The horizontal double line with adjacent arrow between Diversion and Valving indicates the flow of diverted liquid to the bottom of the diverter chamber where the valving is located, as shown in more detail in a subsequent view.

Also provided is Delay of the diversion timing relative to the timing of the valving action. It will be understood that many conventional timers are available for use as illustrated, including provision of a delayed output, adjustable from nil upward, as well as a relatively non-delayed output. The structure of such timer does not constitute any part of this invention, and, thus, is not described further here.

Figure 6:
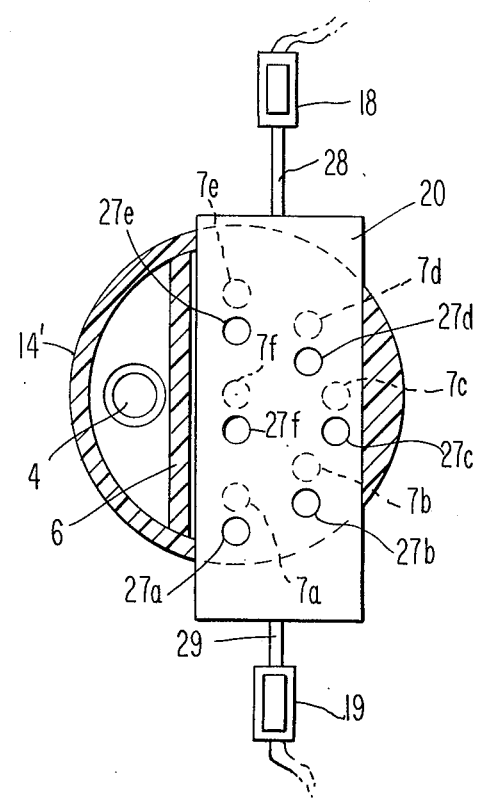
FIG. 6 is a sectional plan taken at VI—VI on FIG. 5.
Figure 5:
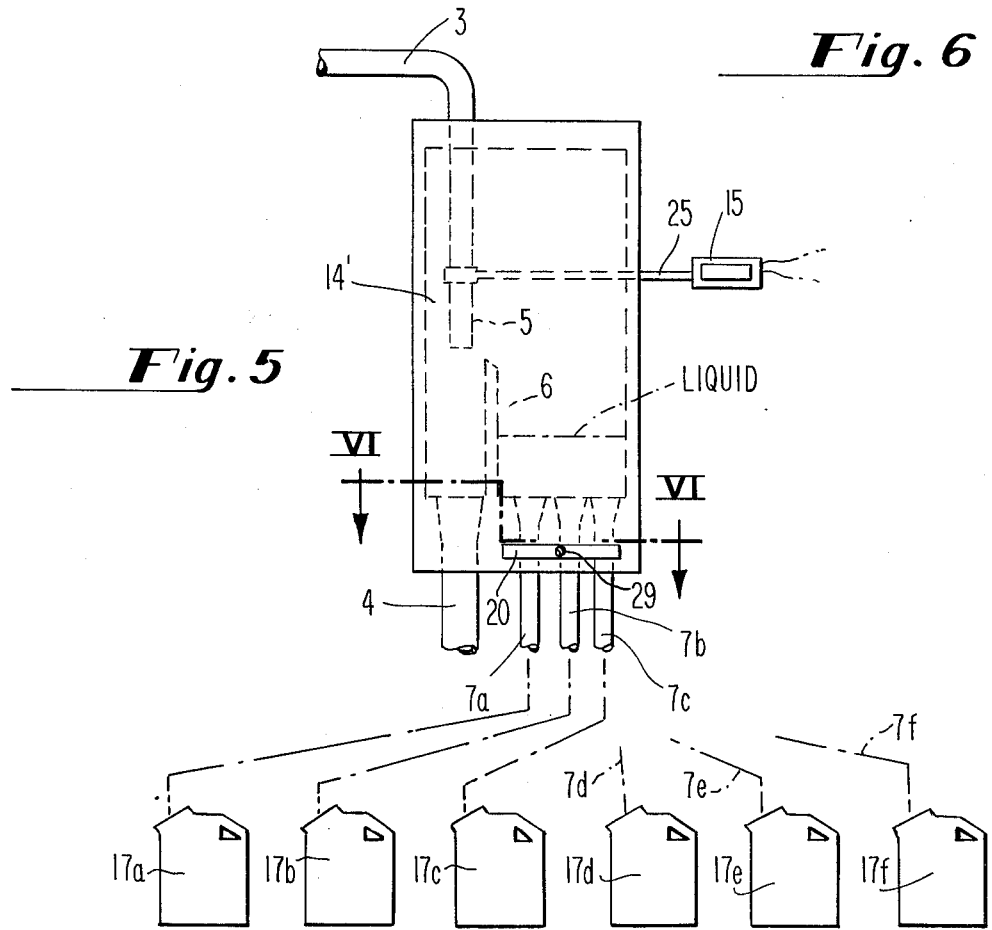
FIG. 5 is a fragmentary schematic side elevation of equipment of preceding views.

FIGS. 4, 5, and 6 show Multiple Diverter Chamber 14' in more detail. In the bottom plan of FIG. 4, the piping from the under side of the chamber is shown sectioned, including return line 4, and sample lines 7a to 7f, inclusive. Valve slide 20 is shown in the open position, i.e., with openings in the slide in their customary condition of registering with the respective sample lines. At opposite ends of the slide (top and bottom in this view) solenoid armature shafts appear, broken away. Also shown fragmentarily in this view are flow line 3 at the left and diversion solenoid armature shaft 25 at the right. FIG. 6, which is sectioned at a higher level, shows slide 20 in alternative closed position, with opening 27a to 27f. "Open" and "close" solenoids 18 and 19 respectively, linked to the slide by respective armature shafts 28 and 29, appear in this view, the latter solenoid being actuated and holding the slide closed momentarily, as will be described further in the summary of operation below.

FIG. 5 shows the apparatus from the side, similar to the view of the single diverter chamber in FIG. 1. Sample lines 7a, 7b, 7c conceal the remaining sample lines from view, but broken lines indicate the distribution of all sample lines to their respective collection bottles 17a to 17f, all of which are shown. Shown in broken lines inside the diverter chamber are tapered inlets (into those lines) within which liquid collects momentarily, such as to the similarly indicated liquid level.

Operation of the disclosed apparatus according to this invention is readily summarized and equally readily understood. A stream of liquid is pumped from the body of liquid to be sampled through the flow line and the flexible inlet tube into the primary compartment of the multiple diverter chamber. The stream of liquid normally flows by gravity out the return line, but the timer actuates the diverter solenoid intermittently to divert the stream momentarily into the secondary compartment of the diverter chamber. The timer also actuates "close" solenoid for the valve slide, which normally is retained in the open position by the open solenoid, to close at about the time of the diversion so that the diverted liquid will be retained momentarily. Then the inlet tube solenoid is deactuated, whereupon the stream of liquid returns to the primary compartment and out the return line. Also, the open solenoid is actuated, and the close solenoid deactuated, returning the valve slide to its normally open position, whereupon the diverted liquid flows from the secondary compartment out the respective sample lines and into the corresponding bottles.

Actuation of the diversion solenoid may be delayed briefly after actuation of the valve slide to favor filling of the tapered inlets of the sample lines before they begin to empty. Such filling is helpful in assuring substantially equal sample volumes as is usually desired. Unequal sample volumes can be obtained where preferred by using dissimilar sizes of sample lines and inlets from the chamber thereto.

Suitable materials of construction for the apparatus of this invention are readily available, being wholly conventional and not forming any part of the invention itself. Polyvinyl chloride (PVC) is a convenient composition for the chamber(s) and lines, which alternatively may be made of tetrafluoroethylene (TFE) or other suitable plastic or even of stainless steel. Various parts of the apparatus may be made of different ones of these or other similarly suitable materials, of course.

Although a single embodiment of this invention has been described and illustrated, modifications may be made therein, as by adding, combining, deleting, or subdividing parts or steps, or substituting equivalents, while retaining at least some of the benefits of the invention, which itself is defined in the following claims.

The invention claimed is:

1. In liquid sampling wherein liquid is withdrawn from a body of liquid being sampled to flow past an intermittent diversion locus and back to the body of liquid or to waste except when being diverted from such locus to a collection location, the improvement in providing a plurality of separate samples simultaneously comprising diverting the flow of liquid temporarily, into a region of confinement, providing a plurality of outlets from such confinement, and separately flowing streams of liquid from the respective outlets to the collection location and collecting them as individual samples thereat, including the steps of closing the outlets during the period of flow diversion and opening them thereafter.

2. Liquid sampling according to claim 1, wherein the outlets are opened at the end of the period of diversion.

3. Liquid sampling according to claim 1, wherein the outlets are opened after a preset delay after the end of the period of diversion.

4. Liquid sampling according to claim 1, wherein once opened the outlets are maintained open until the next period of diversion.

5. Liquid sampling according to claim 1, wherein the outlets are opened and closed by means interposed essentially perpendicular to the flow of liquid.

6. In apparatus for sampling liquid from a body thereof, including means for flowing liquid therefrom past an intermittent diversion locus and back to the body of liquid or to waste except when being diverted from such locus to a collection location, improved means for collecting multiple samples comprising a device for diverting the liquid flow intermittently into a temporarily confining chamber, the chamber having a plurality of outlets therefrom to individual containers, and valve means for closing and opening the outlets in unison.

7. Liquid sampling apparatus according to claim 6, including bypass means for regulating the liquid flow past the diversion locus by bypassing any excess back to the body of liquid or to waste.

8. Liquid sampling apparatus according to claim 6, including timer means for controlling the period of diversion and, thus, the sample volume.

9. Liquid sampling apparatus according to claim 8, including timer means for controlling actuation of the valve means.

10. Liquid sampling apparatus according to claim 9, wherein the same timer means controls actuation of the diverter and valve means.

11. Liquid sampling apparatus according to claim 10, including delay means between the timer and means for actuating the valve means.

12. In apparatus for sampling liquid from a body thereof, including means for flowing liquid therefrom past an intermittent diversion locus and back to the body of liquid or to waste except when being diverted from such locus to a collection location, a chamber for confining the liquid flow temporarily, a first compartment therein having an outlet therefrom back to the body of liquid or to waste, a second compartment therein having a plurality of outlets therefrom to individual containers, and means for diverting the flow of liquid into the chamber from entering the first compartment to entering the second compartment throughout a period of diversion and then returning the undiverted flow to enter the first compartment, the improvement in valve means for closing and opening the outlets from the second compartment comprising a horizontally sliding member having openings vertically therethrough adapted to register with the outlets in the open valve position.

13. Liquid sampling apparatus according to claim 12, wherein the second compartment has a horizontal member over-lying the sliding member of the valve means bored vertically in line with the respective outlets and extending vertically for such a distance that each such bore has a minimum volume of at least about 25 milliliters.

* * * * *